United States Patent
Leitch

(10) Patent No.: US 9,408,633 B2
(45) Date of Patent: Aug. 9, 2016

(54) OBSTETRICAL INSTRUMENT

(71) Applicant: DAYLIGHT OB, LLC, Fort Wayne, IN (US)

(72) Inventor: Rosemary E. Leitch, Fort Wayne, IN (US)

(73) Assignee: DAYLIGHT OB, LLC, Fort Wayne, IN (US)

( * ) Notice: Subject to any disclaimer, the term of this patent is extended or adjusted under 35 U.S.C. 154(b) by 113 days.

(21) Appl. No.: 13/904,528

(22) Filed: May 29, 2013

(65) Prior Publication Data

US 2013/0325027 A1    Dec. 5, 2013

Related U.S. Application Data

(60) Provisional application No. 61/689,357, filed on Jun. 5, 2012.

(51) Int. Cl.
*A61B 17/42* (2006.01)

(52) U.S. Cl.
CPC ....................... *A61B 17/42* (2013.01)

(58) Field of Classification Search
CPC ........... A61B 17/442; A61B 2017/445; A61B 2017/447; A61B 17/44; A47J 43/25
USPC ...................... 606/119–124, 1; 294/183, 189; 15/244.1–244.3; 132/320; 601/136, 601/139; 30/276
See application file for complete search history.

(56) References Cited

U.S. PATENT DOCUMENTS

| | | | | |
|---|---|---|---|---|
| 1,780,155 | A * | 11/1930 | Hahn | D06F 5/02 |
| | | | | 4/255.11 |
| 4,483,636 | A * | 11/1984 | Meyer | 401/266 |
| 5,388,700 | A * | 2/1995 | Per-Lee | 206/581 |
| 5,870,792 | A * | 2/1999 | Shurtliff | 15/102 |
| 6,438,787 | B1 * | 8/2002 | Young | 15/210.1 |
| 2008/0216272 | A1 * | 9/2008 | McLain | 15/230.18 |
| 2011/0196382 | A1 * | 8/2011 | Barrier et al. | 606/123 |

OTHER PUBLICATIONS

Keisha A. Jones et al., Pessary Use in Pelvic Organ Prolapse and Urinary Incontinence, vol. 3 No. 1 2010 Reviews in Obstetrics & Gynecology.

Anthony J. Vlera et al., Practical Use of the Pessary, Am Fam Physician, May 1, 2000.

* cited by examiner

*Primary Examiner* — Jonathan W Miles

*Assistant Examiner* — Majid Jamialahmadi

(74) *Attorney, Agent, or Firm* — Faegre Baker Daniels LLP

(57) ABSTRACT

An obstetrical instrument includes an elongated handle and a fetal head support portion coupled with a distal end of the elongated handle.

27 Claims, 4 Drawing Sheets

OBSTETRICAL INSTRUMENT

CROSS REFERENCE TO RELATED APPLICATIONS

This is a non-provisional application based upon U.S. Provisional Patent Application Ser. No. 61/689,357, entitled "DAYLIGHT UNWEDGE FETAL HEAD LODGED IN BIRTH CANAL", filed Jun. 5, 2012, which is incorporated herein by reference.

BACKGROUND OF THE INVENTION

1. Field of the Invention

The present invention relates to an obstetrical instrument, and, more particularly, to an obstetrical instrument for use during the birthing process.

2. Description of the Related Art

It is not uncommon during the birthing process for a pregnant patient to reach full dilation of the cervix and begin pushing the fetus down through the birth canal only to have the fetus become lodged in the birth canal. Often a vacuum or forceps may be used to further assist the delivery. This may, however, worsen the situation by causing the fetus to become more firmly impacted or lodged in the birth canal without achieving delivery. After attempts of vaginal delivery are abandoned, the delivering physician must deliver the fetus through cesarean section.

During the course of a cesarean section, the fetus must be positioned such that the physician can reach behind the head of the fetus to deliver the baby out of the uterine cavity through an incision made for purposes of delivery. Presently, the fetal head is often positioned for such delivery by an assisting physician or nurse. Such an assistant must insert his or her hand up through the birth canal and place his or her fingers against the fetal head to position the head such that the delivering physician can reach behind the head and gently deliver the baby out through the incision in the uterine cavity. Often in such cases, a surgical drape is placed over the legs of the patient and the assistant is essentially working blind under the sterile drape.

The assistant who asserts the force to push the fetal head into position for the delivering physician does so with his or her fingers, which requires considerable force and is limited by the length of the assistant's arms and/or fingers, as well as by the assistant's physical strength.

What is needed in the art is an obstetrical device which provides for a more efficient and safe delivery of a fetus.

SUMMARY OF THE INVENTION

The present invention provides an obstetrical instrument, namely, a fetal head elevator, including an elongated handle and a fetal head support portion coupled with a distal end of the elongated handle.

The invention further provides an obstetrical instrument, namely, a fetal head elevator including an elongated handle, an intermediate member coupled with a distal end of the elongated handle, and a fetal head support portion coupled with the intermediate member.

Additionally, the present invention further provides a method of repositioning the head of a fetus during the birthing process. According to the method of the present invention, an obstetrical instrument, namely a fetal head elevator, is provided which includes an elongated handle and a fetal head support portion coupled with a distal end of the elongated handle. A distal end of the obstetrical instrument, namely the fetal head elevator, is inserted into the birth canal of a patient and is positioned such that the fetal head support portion of instrument is directly adjacent to the head of the fetus. A controlled pressure is then applied against the fetal head to reposition the fetal head from birth canal into the uterine cavity.

An advantage of the present invention is that the inventive obstetrical instrument allows for the fetal head to be safely repositioned from the birth canal into the uterine cavity for delivery via cesarean section.

Another advantage is that since the inventive obstetrical instrument allows for the fetal head to be elevated, the delivering practitioner is able to easily reach behind the head for a quick delivery with minimized risk of injury to the fetus and to the patient.

A further advantage of the obstetrical instrument of the present invention is that the user can use two hands to exert a controlled pressure to slowly elevate the head of the fetus into position for a delivering physician to efficiently and safely deliver the fetus through an incision in a cesarean section.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
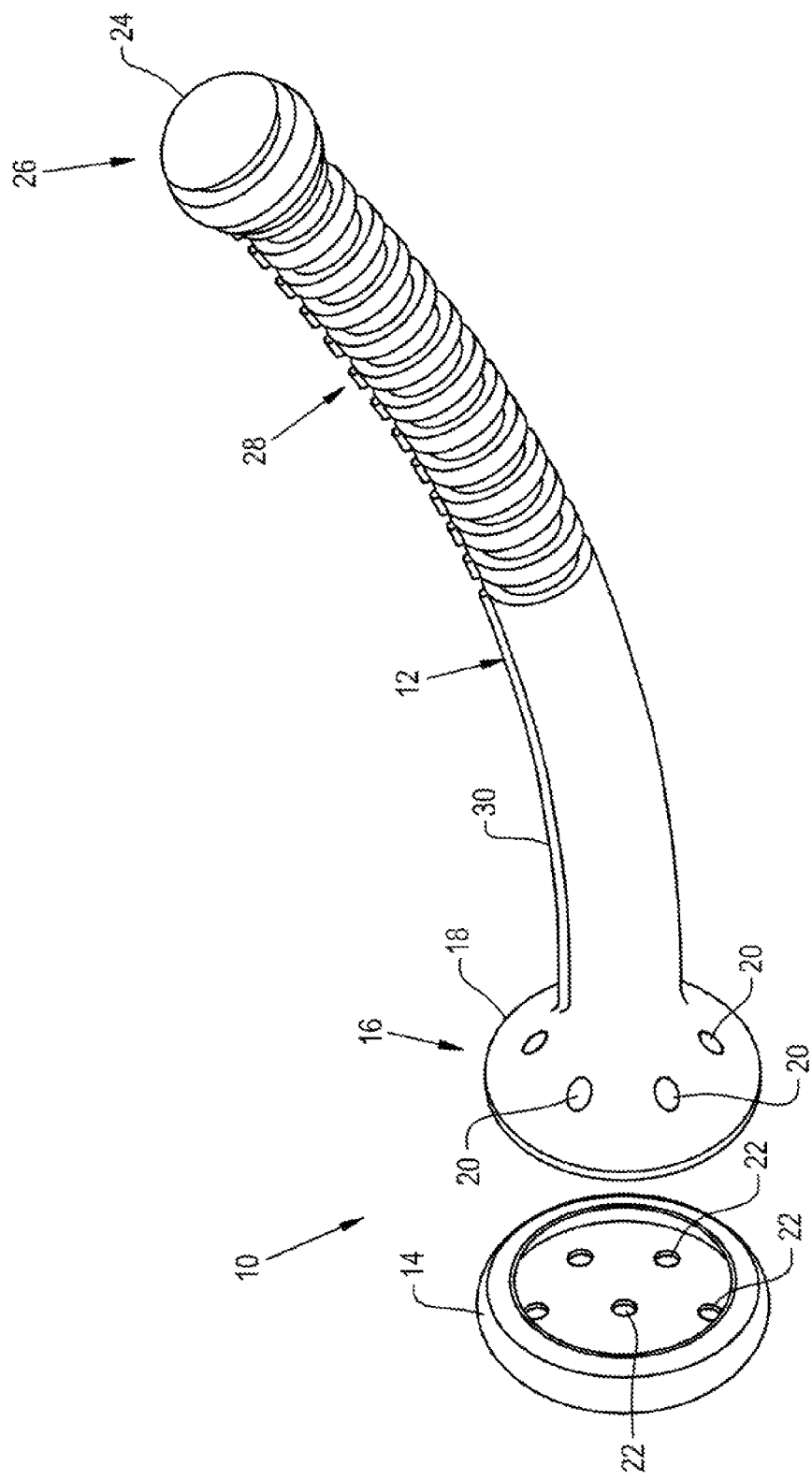
FIG. 1 is a perspective view of an embodiment of an obstetrical instrument according to the present invention.
Figure 2:
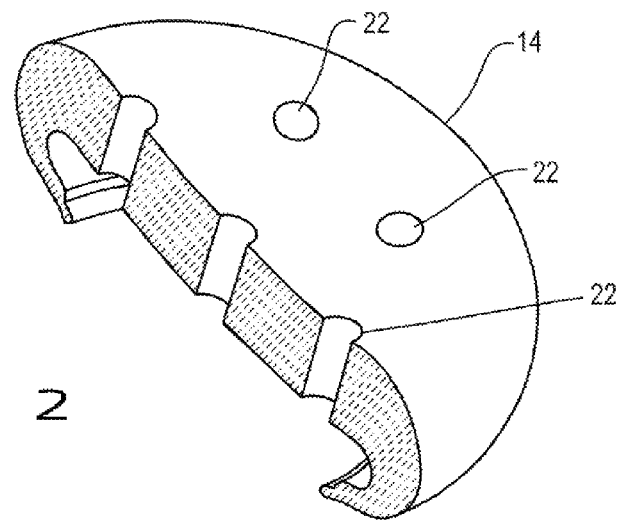
FIG. 2 is a cross-sectional view of a fetal head support portion of the obstetrical instrument of FIG. 1.

Referring now to the drawings, and more particularly to FIGS. 1 and 2, there is shown an obstetrical instrument 10, namely a fetal head elevator 10, which generally includes an elongated handle 12 and a fetal head support portion 14 (shown in cross section in FIG. 2).

At a distal end 16 of handle 12 is a flared portion 18 including a plurality of openings 20 extending therethrough. The plurality of openings 20 may be positioned in any arrangement around the flared portion 18. Fetal head support portion 14 also includes a plurality of openings 22 extending therethrough. The plurality of openings 22 of fetal head support portion 14 are arranged such that when fetal head support portion 14 is coupled with handle 12, they are in fluid connection with the plurality of openings 20 extending through flared portion 18 of handle 12. The plurality of openings 22 of fetal head support portion 14 may, for example, be arranged to align with the plurality of openings 20 extending through flared portion 18 of handle 12.

Alternatively, or in addition, a channel (not shown) may be formed within flared portion 18 such that it intersects with each of the plurality of openings 20 in flared portion 18 of handle 12 such that, regardless of the position of fetal head support portion, the plurality of openings 22 extending therethrough are in alignment with the channel (not shown), and thus in fluid connection with the plurality of openings 20 extending through flared portion 18 of handle 12. Advantageously, the obstetrical instrument according to the present invention allows for fluid, for example air, to flow freely through the obstetrical instrument 10 such that no vacuum is created between obstetrical instrument 10 and the head of a fetus during use by a practitioner.

Fetal head support portion 14 is coupled, for example fixedly coupled or releasably coupled, with distal end 16 of elongated handle 12. More specifically, fetal head support portion 14 is coupled with flared portion 18. Any of a number of known mechanisms may be utilized for coupling distal end 16 of elongated handle 12 with fetal head support portion 14. Fetal head support portion 14 may, for example, be coupled with elongated handle 12 with an adhesive. Alternatively, corresponding male and female threads (not shown) included on the distal end 16 of elongated handle 12 and fetal head support portion 14 may be utilized to releasably couple the components. Fetal head support portion 14 may further include a fixation ring and/or at least one flange for affixing it to distal end 16 of elongated handle 12.

Further, according to the present invention, fetal head support portion 14 is formed of a flexible material configured to cushion and support the head of a fetus while obstetrical instrument 10 is in use. The flexible material must be sufficiently flexible or resilient such that damage to the fetal head is avoided despite the application of pressure across the surface area of the fetal head support portion 14. The flexible material may, for example, have a Shore A hardness in a range between approximately 30 and 50. If the flexible material is a foam, the foam density is, for example, between approximately 3 and 5 pounds per cubic foot (lb/ft$^3$). The fetal head support portion 14 may, for example, be formed of or covered with a sterile foam material and/or sponge material. Exemplary materials from which the fetal head support portion 14 may be covered with or formed of include polyurethane foam, cotton, rayon, polyester or any resilient antimicrobial foam. The fetal head support portion 14 is substantially disc-shaped such that when the obstetrical instrument 10 is in use force exerted by the user of the device is spread across the disc's surface area, rather than focused at a single point, such as is the case, for example if a practitioner must use his or her finger(s) to reposition the head of a fetus.

Handle 12 of obstetrical instrument 10 may be formed of any material known in the art for surgical instruments. For example, the handle may be formed of stainless steel, urethane, silicone, polyurethane, titanium or other known surgical grade polymers and metals. Elongated handle 12 is formed such that it has a gentle curve to accommodate the natural curvature of a pelvis. Elongated handle 12 may further include a bulbous portion 24 at a proximal end 26 of handle 12. Bulbous portion 24 advantageously helps to assure that the user's hand does not slip off of obstetrical instrument's 10 handle 12 during use. Handle 12 further includes a grip portion 28 which may be in any known configuration in the art which prevents obstetrical instrument 10 from slipping while in use, despite encountering the inevitable moisture from body fluids during the birthing process. For example, grip portion 28 may include a plurality of ridges extending around an outer circumference of handle 12. Handle 12 may also include a ridge 30 extending along a superior aspect of handle 12 in a direction parallel with a longitudinal axis of the elongated handle 12. Ridge 30, or directional ridge 30, serves as a directional indicator to mark the top of the device, thus allowing the individual maneuvering obstetrical device 10 to have a tactile sense of the position of the device for situations when a visual sense of position is not feasible, for example, due to the use of a sterile drape during a cesarean section.

Figure 3:
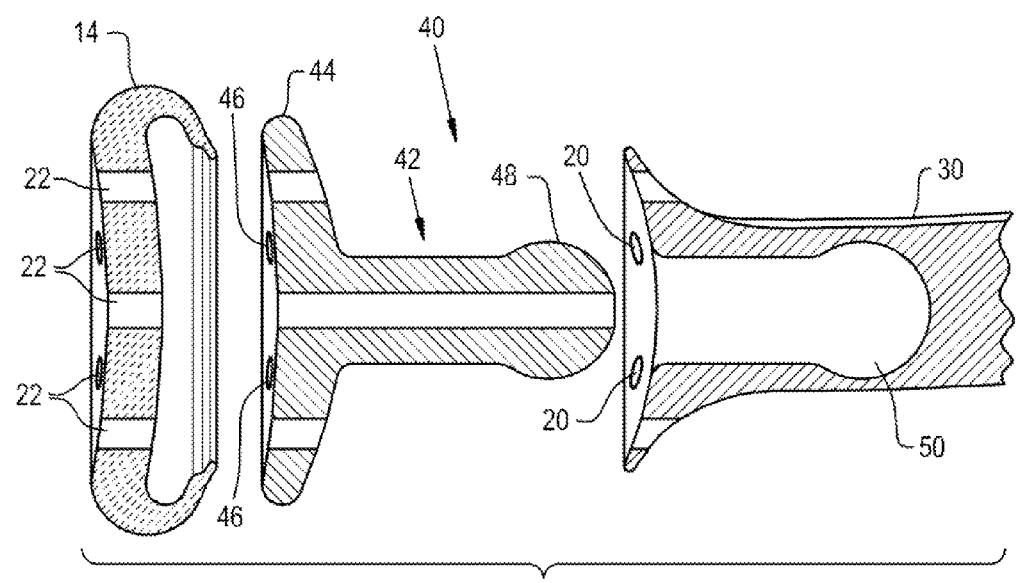
FIG. 3 is an exploded sectional view of a second embodiment of an obstetrical instrument according to the present invention.

Referring now to FIG. 3, there is shown a second embodiment of an obstetrical instrument 40 according to the present invention. Obstetrical instrument 40 has substantially the same structure of the first embodiment of obstetrical instrument 10 discussed more fully above. The primary difference of obstetrical instrument 40 is that an intermediate member 42 is provided which includes a disc-shaped portion 44 which includes a plurality of openings 46 extending therethrough and which are arranged such that they are in fluid alignment with openings 20 in flared portion 18 of handle and openings 22 in fetal head support portion 14 when assembled. Accordingly, in use, the aligned openings (20, 22 and 46) provide a fluid passage such that no vacuum is created between the obstetrical device 40 and the fetal head.

According to this embodiment of obstetrical instrument 40, fetal head support portion 14 is releasably coupled with disc shaped portion 44 of intermediate member 42. It is, however, feasible for fetal head support portion 14 to be fixedly coupled with disc shaped portion 44 of intermediate member, for example using an adhesive. When assembled, intermediate member 42 is fixedly or releasably coupled with distal end 16 of handle 12, for example with flared portion 18 of handle 12.

Intermediate member 42 may be firmly coupled with handle 12 using any number of known coupling or fastening mechanisms, for example a key lock system, a cam system or a ball and socket mechanism, such as that illustrated in FIG. 3. According to the embodiment of obstetrical device 40 illustrated in FIG. 3, intermediate member 42 includes at its proximal end a ball 48 configured for being received in a corresponding socket 50 formed in handle 12.

Figure 4:
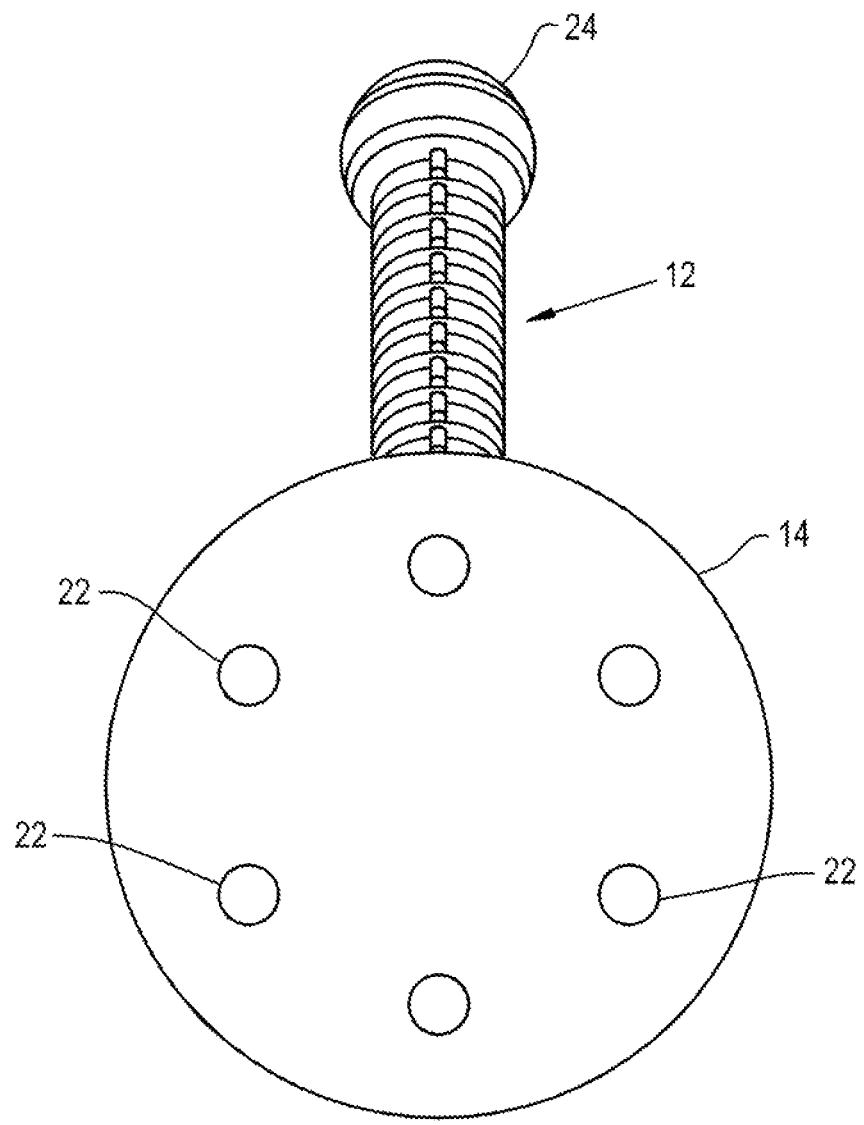
FIG. 4 is an end view of an obstetrical instrument according to the embodiments illustrated in FIGS. 1 and 3.

Referring now to FIG. 4, there is shown an end view of an obstetrical instrument 10 or 40 which clearly illustrates a plurality of openings 22 in fetal head support portion 14. Although openings 22 are arranged in a generally circular pattern around a central point of the generally disc-shaped fetal head support portion 14, openings 22 may be arranged in any number of ways, as long as they are in fluid communication with corresponding openings in the intermediate member 42 and/or flared portion 18 of handle 12, depending upon the embodiment. The edge of the fetal head support portion 14 which would come into contact with a patient's vaginal tissue and/or bladder is sufficiently smooth such that it easily slides along the tissue, thus preventing injury to the bladder and/or vaginal tissue of the birth canal.

Figure 5:
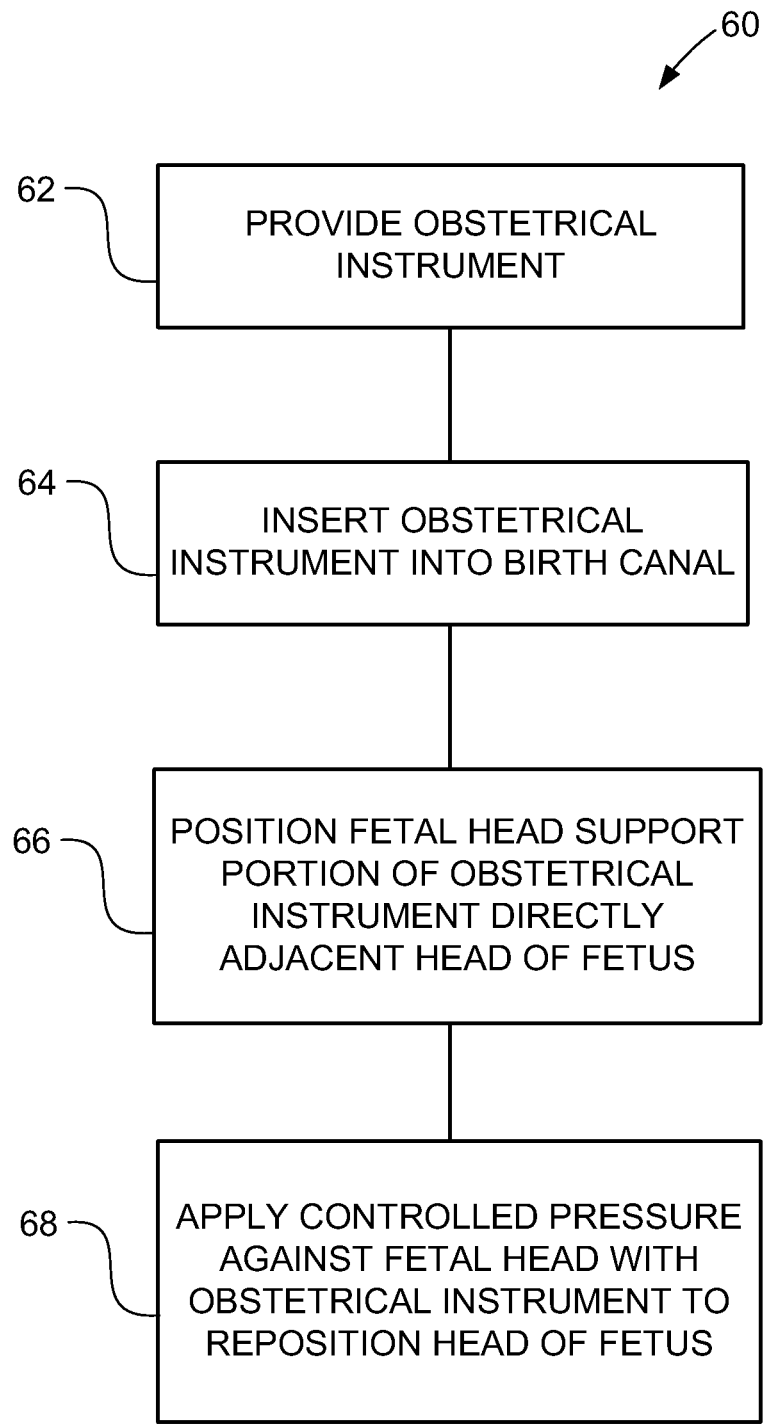
FIG. 5 is a flow chart of a method of repositioning the head of a fetus during the birthing process.

The present invention further provides a method 60 of repositioning the head of a fetus during the birthing process, in other words during childbirth. Referring now to FIG. 5, there is shown a flow chart illustrating the steps of the method 60 according to the present invention. An obstetrical instrument is provided at step 62 which includes an elongated handle and a fetal head support portion coupled with a distal end of the elongated handle. A distal end of the obstetrical instrument is inserted into the birth canal of a patient at step 64. The fetal head support portion of the obstetrical instrument is positioned directly adjacent the head of a fetus at step 66. A controlled pressure is applied against the fetal head with the obstetrical instrument at step 68 to reposition the head of the fetus through the birth canal into the uterine cavity. The obstetrical instrument allows the user to ease the act of elevating the fetal head for purposes of delivery through a cesarean section. More specifically, the obstetrical instrument allows the user to slowly push the fetal head up to the point where a delivering physician can reach below the fetal head and complete the delivery.

Although the obstetrical instrument of the present invention has been described for use in a childbirth environment, it may have additional applications in the veterinary field for the comparative birthing process.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An obstetrical instrument, comprising:
   an elongated handle; and
   a flared portion extending from said elongated handle, said flared portion having a distal face sized and structured to support and elevate a fetal head, the elongated handle having a length sized to allow pressure to be applied from a user's hand holding the handle to the fetal head to reposition the fetal head through a birth canal into a uterine cavity, whereby the fetal head can be supported and elevated by the flared portion in the birth canal prior to delivery, the distal face defining a perimeter, said flared portion defining a fluid flow path from said distal face of said flared portion to an exterior of said flared portion, said fluid flow path presenting a gap in the distal face within the perimeter of the distal face so that, with the instrument positioned to support and elevate the fetal head, the gap defines an area within the perimeter of the distal face that does not contact the fetal head, the distal face defining a contact surface area within the perimeter available to contact the fetal head, the contact surface area larger than an area of the gap, whereby a fetal head elevating force transmitted through the obstetrical instrument is spread across the contact surface area and whereby the fluid flow path resists formation of a vacuum between the obstetrical instrument and a fetal head supported by the obstetrical instrument.

2. The obstetrical instrument of claim 1, wherein said flared portion defines an opening extending through the flared portion to define the fluid flow path from said distal face of said flared portion to an exterior of said flared portion, said opening defining said gap in the distal face within the perimeter of the distal face.

3. The obstetrical instrument according to claim 2, further comprising a fetal head support portion releasably coupled with said flared portion, wherein said fetal head support portion includes an opening extending therethrough and arranged to align with said opening in said flared portion extending from said elongated handle.

4. The obstetrical instrument of claim 1, further comprising:
   a fetal head support portion releasably coupled with said flared portion.

5. The obstetrical instrument of claim 4, wherein said fetal head support portion comprises a foam material.

6. The obstetrical instrument according to claim 4, wherein said fetal head support portion is one of formed of and covered with at least one of a foam material and a sponge material.

7. The obstetrical instrument according to claim 4, wherein said fetal head support portion includes at least one of a fixation ring and at least one flange which affixes said fetal head support portion to said flared portion.

8. The obstetrical instrument according to claim 4, wherein said fetal head support portion is formed of a flexible material and is configured to cushion and support the fetal head while the obstetrical instrument is in use.

9. The obstetrical instrument according to claim 8, wherein said flexible material has a Shore A hardness in a range between approximately 30 and 50.

10. The obstetrical instrument of claim 1, wherein said elongated handle of the obstetrical instrument is curved to accommodate a natural curvature of a pelvis.

11. The obstetrical instrument of claim 1, wherein said flared portion extending from said elongated handle comprises an intermediate member selectively coupled with a distal end of said elongated handle.

12. The obstetrical instrument of claim 11, wherein said intermediate member is releasably coupled with said elongated handle with a ball and socket joint.

13. The obstetrical instrument of claim 11 wherein said the distal end of said elongated handle comprises a handle flared portion.

14. The obstetrical instrument according to claim 13, wherein said intermediate member is releasably coupled with said elongated handle with a ball and socket joint.

15. The obstetrical instrument of claim 1, wherein said flared portion extending from said elongated handle comprises an intermediate member selectively coupled with a distal end of said elongated handle and said distal end of said elongated handle comprises a handle flared portion, said intermediate member defining an opening extending through the intermediate member, said handle flared portion defining an opening extending through the handle flared portion and aligned with the opening extending through the intermediate member to define the fluid flow path from said distal face of said flared portion to an exterior of said flared portion.

16. The obstetrical instrument of claim 1, wherein said flared portion defines a plurality of openings extending through said flared portion, said plurality of openings together defining said gap in the distal face within the perimeter of the distal face.

17. The obstetrical instrument according to claim 1, wherein said elongated handle has a proximal end including a bulbous portion.

18. The obstetrical instrument according to claim 1, wherein said elongated handle includes a grip portion having a plurality of ridges extending around a circumference of said handle.

19. The obstetrical instrument according to claim 1, wherein said elongated handle includes a ridge extending along a superior aspect of said handle in a direction parallel with a longitudinal axis of said elongated handle.

20. A method of repositioning the head of a fetus, the method comprising the steps of:
   inserting a distal end of an obstetrical instrument into a birth canal of a patient, the obstetrical instrument comprising;
      an elongated handle; and
      a flared portion extending from said elongated handle, said flared portion having a distal face;
   positioning said flared portion of said obstetrical instrument to support a fetal head; and
   applying a fetal head elevating pressure against the fetal head with the flared portion of the obstetrical instrument to reposition the fetal head through the birth canal into a uterine cavity of the patient.

21. The method of repositioning the head of a fetus of claim 20, wherein the distal face of the flared portion of the obstetrical instrument defines a perimeter, the flared portion defining a fluid flow path from the distal face of the flared portion to an exterior of the flared portion, the fluid flow path presenting a gap in the distal face within the perimeter of the distal face, whereby during said step of applying a fetal head elevating pressure against the fetal head, the gap defines an area within the perimeter of the distal face that does not contact the fetal head, whereby the fluid flow path resists formation of a vacuum between the obstetrical instrument and the fetal head during said step of applying a fetal head elevating pressure against the fetal head.

22. The method of repositioning the head of a fetus of claim 21, wherein the flared portion extending from the elongated handle comprises an intermediate member selectively coupled with a distal end of the elongated handle and the distal end of the elongated handle comprises a handle flared portion, the intermediate member defining an opening extending through the intermediate member, the handle flared portion defining an opening extending through the handle flared portion and aligned with the opening extending through the intermediate member to define the fluid flow path from the distal face of the flared portion to an exterior of the flared portion.

23. The method of repositioning the head of a fetus of claim 21, wherein the distal face of the flared portion of the obstetrical instrument defines a contact surface area within the perimeter available to contact the fetal head, the contact surface area larger than an area of the gap, whereby during said step of applying a fetal elevating pressure against the fetal head, the fetal head elevating pressure is spread across the contact surface area.

24. The method of repositioning the head of a fetus of claim 23, wherein the flared portion of the obstetrical instrument defines an opening extending through the flared portion to define the fluid flow path from the distal face of the flared portion to an exterior of the flared portion, the opening defining the gap in the distal face within the perimeter of the distal face.

25. The method of repositioning the head of a fetus of claim 20, wherein the obstetrical instrument further comprises a fetal head support portion releasably coupled with said flared portion.

26. The method of repositioning the head of a fetus of claim 20, wherein the elongated handle of the obstetrical instrument is curved to accommodate a natural curvature of a pelvis.

27. The method of repositioning the head of a fetus of claim 20, wherein the flared portion extending from the elongated handle of the obstetrical instrument comprises an intermediate member selectively coupled with a distal end of the elongated handle.

* * * * *